US005858679A

United States Patent [19]
Fornace, Jr. et al.

[11] Patent Number: 5,858,679
[45] Date of Patent: Jan. 12, 1999

[54] METHOD FOR DETERMINING THE PRESENCE OF FUNCTIONAL P53 BY MEASURING GADD45 PROTEIN EXPRESSION

[76] Inventors: Albert J. Fornace, Jr., 9008 Kirkdale Rd., Bethesda, Md. 20817; Michael B. Kastan, 3910 Esgarthway, Owings Mill, Md. 21117; France Carrier, 5225 Pooks Hill Rd., #920-S, Bethesda, Md. 20814-2018

[21] Appl. No.: 432,176
[22] PCT Filed: Nov. 12, 1993
[86] PCT No.: PCT/US93/11026
§ 371 Date: May 10, 1995
§ 102(e) Date: May 10, 1995
[87] PCT Pub. No.: WO94/11533
PCT Pub. Date: May 26, 1994

Related U.S. Application Data

[63] Continuation-in-part of Ser. No. 974,960, Nov. 12, 1992, abandoned.
[51] Int. Cl.$^6$ ............................. G01N 33/53; C07K 15/28
[52] U.S. Cl. ............................................. 435/7.1; 530/386
[58] Field of Search ......................... 435/7.1, 6; 530/386, 530/388.1

[56] References Cited

PUBLICATIONS

Papathanasiou et al, Mol. Cell. Biol 11(2): 1009–1016 (1991).
Green et al, Nucl. Acid. Res 16(1):369 (1988).
Vunakis et al, Meth.Enzymol. 70:49–71 (1984).
Kilpatrick et al, Hybridoma 14(4):355–359, 1995.
M.C. Hollander et al., (Nov. 8, 1993) Analysis of the Mammalian GADD45 Gene and its Response to DNA Damage; *Chemical Abstracts*, vol. 119, No. 19, pp. 230–231 and *J. Biol. Chem.* (1993) 268:24385–24393.
M.B. Kastan et al., (Feb. 1, 1993) A Mammalian Cell Cycle Checkpoint Pathway Utilizing p53 and GADD45 is Defective in Ataxia–Telangiectasia; *Chemical Abstracts*, vol. 118, No. 5., p. 308 and *Cell* (1992) 71:587–597.
B.D. Price et al., (Aug. 17, 1992) GADD45 and GADD153 Messenger RNA Levels are Increased During Hypoxia and After Exposure of Cells to Agents Which Elevate the Levels of the Glucose–Regulated Proteins;*Chemical Abstracts*, vol. 117, No. 17, p. 561 and *Cancer Res.* (1992) 52: 3814–3817.

M.A. Papathanasiou et al., (Sep. 16, 1991) Induction by Ionizing Radiation of the GADD45 Gene Incultured Human Cells: Lack of Mediation by Protein Kinase C; *Chemical Abstracts*, vol. 115, No. 11, p. 419 and *Mol. Cell. Biol.* (1991) 11:1009–1016.
D. Wolf et al., (Nov. 5, 1984) Reconstitution of p53 Expression in a Nonproducer Ab–MuLV–Transformed Cell Line by Transfection of a Functional p53 Gene; *Chemical Abstracts*, vol. 101, No. 19, p. 153 and *Cell.* (1984) 38:119–126.
Kern, et al., Identification of p53 as a Sequence–Specific DNA–Binding Protein; *Science*, 252: 1708–1711 (1991).
Kern et al., Oncogenic Forms of p53 Inhibit p53–Regulated Gene Expression; *Science*, 256:827–83 (1992).
Funk et al., A Transcriptionally Active DNA–Binding Site for Human p53 Protein Complexes; *Mol. Cell Biol.*, 12:2866–2870 (1992).
El–Deiry et al., Definition of a Consensus Binding Site for p53; *Nature Genet*, 1:45–49 (1992).
Kastan et al., Participation of p53 Protein in the Cellular Response to DNA Damage; *Cancer Res.*, 51:6304–6311 (1991).
Kuerbitz, et al., Wild–Type p53 is a Cell Cycle Checkpoint Determinant Following Irradiation; *Proc. Natl. Acad.*, 89: 7491–7495 (1992).
Fornace et al., DNA Damage–Inducible Transcripts in Mammalian Cells; *Proc. Natl. Acad. Sci. U.S.A.*, 85:8800–8804 (1988).
Fornace et al., Mammalian Genes Coordinately Regulated by Growth Arrest Signals and DNA–Damaging Agents; *Mol. Cell. Biol.*, 9:4196–4203 (1989).
Bargonetti et al., Wild–Type but not Mutant p53 Immunopurified Proteins Bind to Sequences Adjacent to the SV40 Origin of Replication; *Cell.*, 65:1083–1091 (1991).

*Primary Examiner*—Eggerton A. Campbell
*Attorney, Agent, or Firm*—Morgan & Finnegan

[57] ABSTRACT

The dependence of ionizing radiation-induced GADD45 mRNA and protein expression on the presence of functional p53 in mammalian cells is disclosed. First and second oligonucleotide sequences are provided which can form a double-stranded oligomer capable of binding to functional p53 protein. The present invention demonstrates that the dependence of ionizing radiation-induced GADD45 mRNA and protein expression on the presence of functional p53 and the binding of functional p53 to a double-stranded oligomer binding sequence can serve as the bases for methods for determining the presence of functional p53 in mammalian cell lines and tumors.

6 Claims, 6 Drawing Sheets

FIG. 2

```
  1       CAT ATG ACT TTG GAG GAA TTC TCG GCT GGA GAG CAG AAG ACC GAA AGG ATG GAT AAG GTG
              1→Met Thr Leu Glu Glu Phe Ser Ala Gly Glu Gln Lys Thr Glu Arg Met Asp Lys Val
 61       GGG GAT GCC CTG GAG GAA GTG CTC AGC GCC AAA GGG GAG CTG AGT CAG CGC ACG ACT GTC GGG
 20 →     Gly Asp Ala Leu Glu Glu Val Leu Ser Ala Lys Gly Glu Leu Ser Gln Arg Thr Ile Thr Val Gly
121       GTG TAC GAA GCG GCC AAG CTC AAC GTC GAT CCC AAC GTG GTG TTG TGC CTG CTG
 40 →     Val Tyr Glu Ala Ala Lys Leu Asn Val Asp Pro Asn Val Val Leu Cys Leu Leu
181       GCG GCG GAC GAG GAC AGA GAT GCT GTG CAG ATC CAC TTC ACC CTG ATC CAG
 60 →     Ala Ala Asp Glu Asp Arg Asp Ala Val Gln Ile His Phe Thr Leu Ile Gln
241       GCG TTT TGC GAG AAC GAC ATC CTG CGC GTC AGC AAC CCG GGC CGG CTG GCG
 80 →     Ala Phe Cys Glu Asn Asp Ile Leu Arg Val Ser Asn Pro Gly Arg Leu Ala
301       GAG CTC CTG GAG ACC TTG GAG GCT GGC CCC GCG AGC GCC GAG CAG CCC
100 →     Glu Leu Leu Glu Thr Leu Glu Ala Gly Pro Ala Ser Ala Glu Gln Pro
361       CCG GAC CTG CAC TGC GTG CTG ACG CAA CAT CCA TCA TCT CAA GAT CCT GCC
120 →     Pro Asp Leu His Cys Val Leu Thr Asn Pro His Ser Gln Trp Lys Asp Pro Ala
421       TTA AGT CAA CTT ATT TGT TTT TGC CGG GAA AGT CGC TAC ATG CGC TGG CAA TGG GTT CCA GTG
140 →     Leu Ser Gln Leu Ile Cys Phe Cys Arg Glu Ser Arg Tyr Met Arg Trp Gln Trp Val Pro Val
                                              BamHI site
481       ATT AAT CTC CCT GAA CGG TGA AGATCA
160 →     Ile Asn Leu Pro Glu Arg  . . .
```

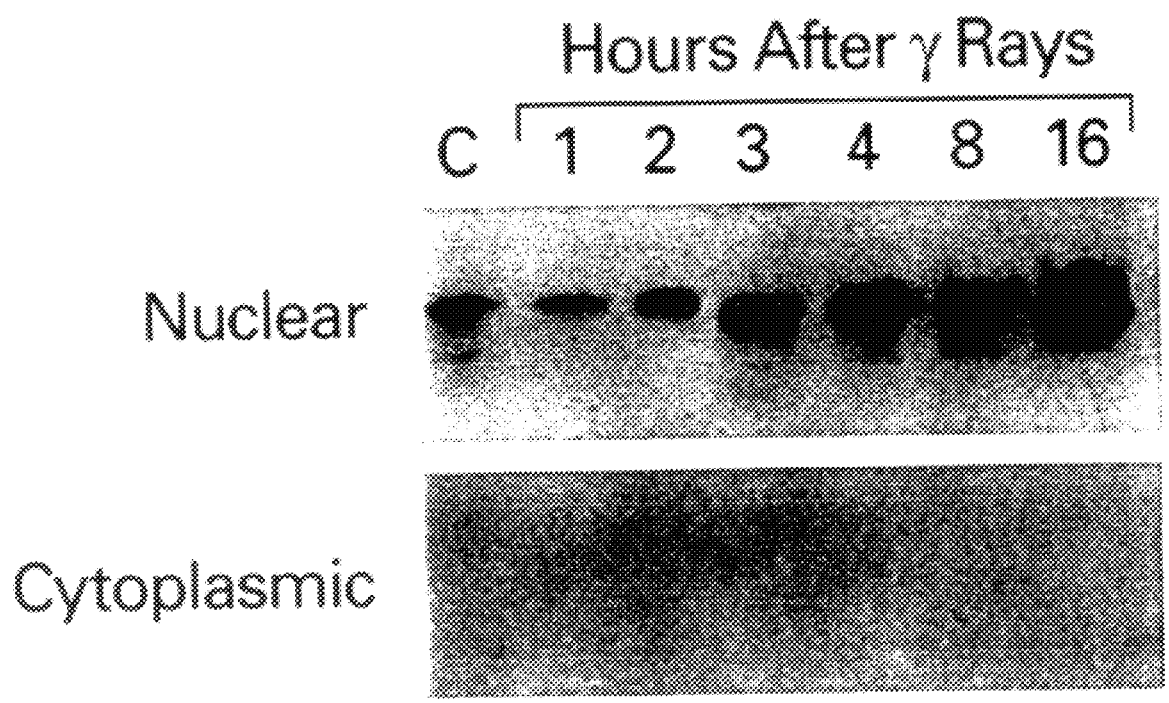

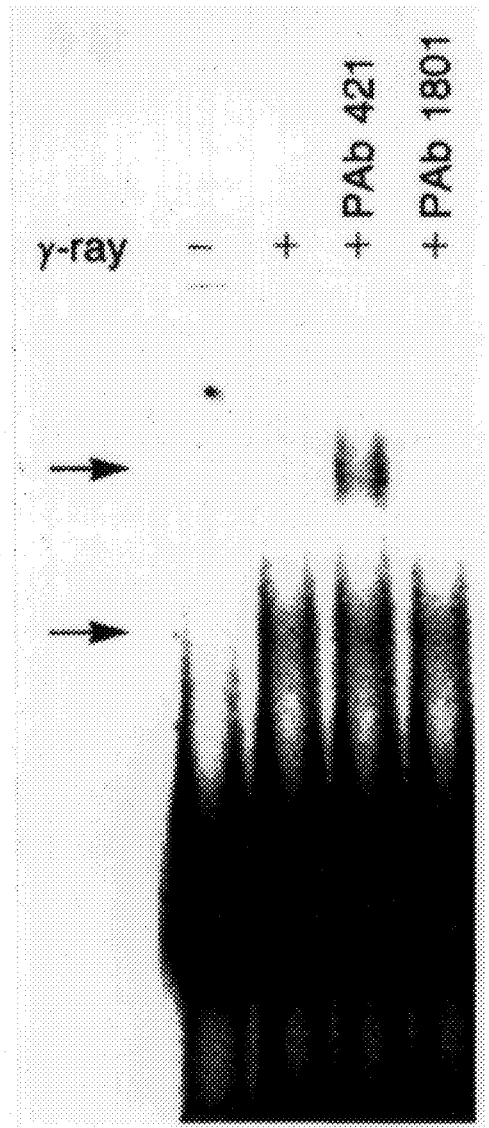

METHOD FOR DETERMINING THE PRESENCE OF FUNCTIONAL P53 BY MEASURING GADD45 PROTEIN EXPRESSION

The present application is a national filing of PCT International Application No. PCT/US93/11026 filed Nov. 12, 1993, which is a CIP of U.S. Ser. No. 07/974,960 filed Nov. 12, 1992, now abandoned

FIELD OF THE INVENTION

This invention is in the field of tumor cell biology. More specifically, this invention relates to the first identification of a gene, GADD45, whose expression has been shown to be altered by the presence of functional p53 protein and to the development of methods for determining the presence of functional p53 protein in mammalian cells.

BACKGROUND OF THE INVENTION

The p53 protein was first detected in a complex with the SV40 large T antigen in rodent cells transformed by simian virus SV40 (Lane, D. P. et al. (1979) Nature, 278:261–263). Subsequently, p53 was shown to be complexed with adenovirus and oncogenic papillomavirus oncoproteins (Sarnow, P. et al. (1982) Cell, 28:387–394; Werness, B. A. et al. (1990) Science, 248:76–79). Initially, p53 protein was considered to be a cellular proto-oncogene but recent observations have indicated that the gene encoding p53 in its native form is a tumor suppressor gene. Experimental support for the role of p53 as a tumor suppressor has been provided by the demonstration that the p53 gene can suppress the growth of transformed murine or human cells and that mutation or deletion of the p53 gene results in loss of this suppressor function (Eliyahn, D. et al. (1989) Proc. Natl. Acad. Sci. U.S.A., 86:8763–8767; Baher, S. J. et al. (1990) Science, 249:912–915; Mercer, W. E. et al. (1990) Proc. Natl. Acad. Sci. U.S.A., 87:6166–6170). To date, such mutations of the p53 gene have been demonstrated in tumors of the colon, breast, lung, ovary, bladder, and several other organs, making the p53 gene the most commonly mutated gene yet identified in human cancers (Vogelstein, B., (1990) Nature, 348:681–682). Based on the association of tumor progression with alterations in the p53 gene, major research efforts have been devoted to elucidating the potential biological function of p53.

Recent evidence strongly suggests that one function of p53 protein may be in the regulation of gene transcription. Several groups have demonstrated sequence-specific binding of p53 to DNA (Bargonetti et al. (1991) Cell, 65:1083–1091); Kern et al. (1991) Science, 252:1708–1711) and a genomic consensus sequence has been elucidated that consists of two copies of a symmetric 10 base pair (bp) motif separated by 0–13 bp (El-Deiry et al. (1992) Nature Genet., 1:45–49). Placement of this consensus sequence adjacent to a basal promoter linked to chloramphenicol acetyltransferase (CAT) or luciferase reporter genes resulted in induction of the reporter gene when these constructs were cotransfected with a p53 expression vector into mammalian cells (Kern et al. (1992) Science, 256:827–830; Funk W. D. et al. (1992) Mol. Cell. Biol., 12:2866–2871). In addition, the amino-terminus of p53 has been shown to behave as an acidic transcriptional activation domain when fused to GAL4 (Fields, S. et al. (1990) Science, 249:1046–1049).

More recently, wild-type (wt) p53 protein has been shown to directly activate transcription in vitro (Farmer, G. et al. (1992) Nature, 358:83–86). However, despite the experimental evidence supporting a role for p53 protein in transcriptional activation and the high interest in the potential involvement of p53 in tumorigenesis, there are currently only a few methods available for determining the presence of wt or mutant p53 protein in mammalian cells. One widely used method involves laborious DNA sequencing of the p53 gene itself. A major drawback of this approach is that the presence of a normal p53 DNA sequence is not necessarily an accurate predictor of the presence of functional p53 protein in the cells assayed since interference of p53 function by viral proteins or by abnormal binding of p53 protein to endogenous cellular proteins can occur (Momand, J. et al. (1992) Cell, 69:1237–1245; Oliner, J. D. et al. (1992) Nature, 358:80–83). In addition, this approach is both costly and time-consuming.

Another method used for determining the presence of wt or mutant p53 involves the use of antibodies capable of distinguishing between these two forms of p53. However, this approach also has several limitations. First, many of the mutations which arise in the p53 protein are point mutations and not all such mutations would be expected to be distinguished by a limited number of antibodies. Second, since p53 is the most commonly mutated protein identified in human cancers, the number of antibodies necessary to detect all of the different mutant forms of p53 may be quite high; therefore, this method would be impractical and costly. Finally, the use of anti-p53 antibodies to determine the presence of functional p53 in the cell is not an accurate predictor of functional p53 presence for the reasons cited above for the DNA sequencing method. Therefore, while currently used assays can detect the presence of wild-type or mutant p53 protein in mammalian cells, they cannot accurately determine the presence of functional p53 protein in these cells.

One potential approach to developing a method for determining the presence of functional p53 protein in mammalian cells would be to identify a specific gene whose expression is dependent on the presence of functional p53. Recent studies demonstrating a role for p53 protein in the G1 arrest of the cell cycle following damage of DNA by ionizing radiation (Kastan, N. B. et al. (1991) Cancer Res., 51:6304–6311; Kuerbitz, S. J. et al. (1992) Proc. Natl. Acad. Sci. U.S.A., 89:7491–7495). These studies suggested that genes that are differentially regulated after DNA damage and growth arrest may be candidates for p53-inducible genes.

Five gadd (growth-arrest and DNA-damage inducible) genes have been isolated on the basis of induction after DNA-damage in Chinese hamster ovary (CHO) cells. Subsequently, these genes were found to be induced by DNA-damaging agents or other treatments eliciting growth-arrest, such as serum reduction, in a wide variety of mammalian cells (Fornace, A. J. et al. (1989a) Mol. Cell. Biol., 9:4196–4203). In particular, the GADD45 and GADD153 genes have been found to be rapidly and coordinately induced by agents such as methyl methanesulfonate (MMS) that produce high levels of base damage in DNA in every cell line examined, including human, hamster, murine, and rat cells (Fornace, A. J. et al., (1989a); Fornace, A. J. et al. (1992) Ann. NY Acad. Sci., 26:505–524). Recently, the human GADD45 gene was found to be rapidly induced by ionizing radiation (IR) in lymphoblasts and fibroblasts (Papathanasiou, M. A. et al., (1991) Mol. Cell Biol., 11:1009–1016)). This IR response appeared to be distinct from the "gadd" response to MMS and other base-damaging agents because only GADD45 was strongly induced, and induction occurred with doses of IR that produced relatively little DNA base damage. In addition, a recent report (Fornace, A. J. et al. (1991) in Chapman, J. D., Dewey, W. C., Whitmore, G. F. (eds): "In Radiation Research: A Twentieth-Century Perspective", Academic Press, San Diego, p. 213) demonstrated that IR induction of GADD45 is absent in some human tumor cell lines. Taken together, this information suggests a potential role for p53 in the IR response of GADD45.

SUMMARY OF THE INVENTION

The invention includes three methods for determining the presence of functional p53 protein in mammalian cells. The first two methods for determining the presence of functional p53 in mammalian cells measure either GADD45 mRNA expression or expression of the GADD45 protein.

In the third method, two nucleic acid sequences are utilized. The first nucleic acid sequence has the sequence according to SEQ ID No. 1 and the second has the sequence according to SEQ ID NO. 2. SEQ ID NO. 1 and SEQ ID NO. 2 are complementary sequences found in the third intron of the human GADD45 gene and SEQ ID NO. 1 and SEQ ID NO. 2 can form a double-stranded nucleic acid sequence capable of binding to functional p53 protein. The presence of functional p53 protein in mammalian cells is determined by measuring binding of mammalian cell protein extracts with the double-stranded nucleic acid sequence.

DESCRIPTION OF FIGURES

FIG. 2 shows the nucleic acid sequence of the PCR-amplified GADD45 cDNA insert which was inserted into the NdeI-BamHI restriction sites of the pET-14-b vector to produce the recombinant GADD45 expression vector. The NdeI and BamHI restriction sites indicated at the 5' and 3' ends of the GADD45 nucleic acid insert were introduced during PCR amplification. The amino acid residues encoded by the insert are shown below the nucleic acid sequence.

FIG. 4 shows the results of a Western blot in which nuclear and cytoplasmic protein extracts from γ-irradiated and unirradiated human colorectal carcinoma cells were analyzed for the presence of GADD45 protein using purified anti-GADD45 polyclonal antibody.

FIGS. 5A and 5B show mobility-shift assays with a double-stranded oligomer containing a p53-binding site and nuclear extracts from irradiated cells. FIG. 5A. Nuclear extracts from irradiated or unirradiated ML-1 cells were incubated with labeled DNA corresponding to the human GADD45 p53-binding site, and the resulting DNA-protein complexes were electrophoresed in a neutral acrylamide gel and visualized by autoradiography. FIG. 5B. In a separate experiment, a similar analysis was carried out using nuclear extracts from irradiated or unirradiated ML-1 or HL-60 cells. The first 3 lanes consist of controls where probe alone (lanes 1 and 2) or probe with antibody to p53 (lane 3) were used in the absence of nuclear extracts. The lower arrow indicates the position of the IR-induced band and the upper arrow indicates the position of the super-shifted band seen with the antibody to p-53, PAb421.

DETAILED DESCRIPTION OF THE INVENTION

Figure 1A:
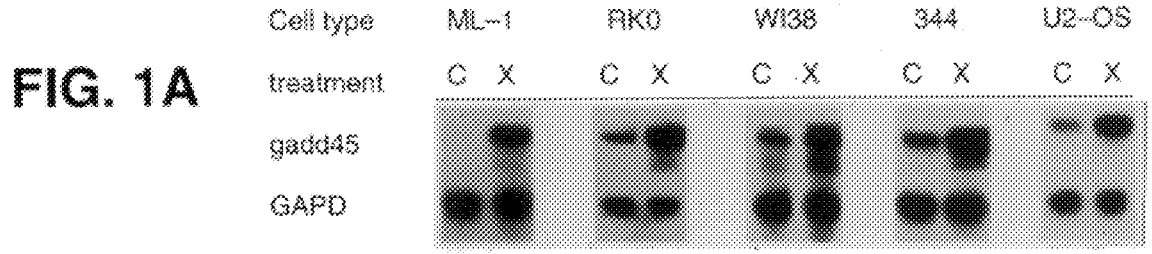
FIGS. 1A–C show the relationship of p53 phenotype to the γ-ray response of GADD45. A. RNA from γ-irradiated (X) and unirradiated (C) human cell lines with a wtp53 phenotype were analyzed by RNase protection assay using probes complementary to human GADD45 and glyceraldehyde-3-phosphate dehydrogenase (GAPD) mRNA. B. Human tumor cell lines with a mutant or null p53 phenotype were analyzed as in (A). C. Primary fibroblasts from mice with the designated p53 genotype were irradiated as above and RNA was analyzed by Northern blot using probes complementary to hamster GADD45 and β-actin mRNA.

The present invention relates to identification of GADD45 as a gene whose expression has been shown to be altered by the presence of functional p53 protein in mammalian cells. "Functional p53" means p53 protein which is able to activate gene transcription. More specifically, the invention relates to the identification of GADD45 as a gene that is up-regulated by p53 after treatment of mammalian cells with a specific inducing signal, especially ionizing radiation. The invention further relates to methods of determining the presence of functional p53 protein in mammalian cells based on the dependence of IR-induced GADD45 mRNA and protein expression on the presence of functional p53.

In one embodiment of the invention, the method to detect functional p53 comprises:
(a) stimulating mammalian cells to increase expression of GADD45 mRNA; and
(b) comparing the level of GADD45 mRNA in stimulated cells to the level of GADD45 mRNA in unstimulated cells.

Examples of mammalian cells that can be used in the present invention are transformed mammalian cell lines. Such cell culture lines include, but are not limited to, cells of lymphoblast and fibroblast origin. A preferred cell line is the ML-1 lymphoblast cell line. (Kastan, M. B. et al. (1991b) Cancer Res., 51:4279–4286)

In this invention, primary cultures of mammalian cells can also be used. Such cells can be biopsies taken from mammalian tumors, where tumor cells include, but are not limited to, tumor cells of the colon, lung, breast, ovary and bladder. Mammalian cell cultures can be initiated from biopsies by surgical incisional or excisional methods. A preferred method of initiating cell culture lines is via the removal of viable tumor tissue under sterile conditions. In most cases, a needle biopsy containing about $10^6$ to about $10^8$ cells is sufficient to initiate a culture. It is understood by one skilled in the art that the number of tumor cells required to initiate and establish a cell culture line depends on the individual tumor to be examined. In a preferred embodiment, certain tumor cells are cultured short-term (2 days to 20 days) using standard cell and tissue culture techniques ("Selected Methods in Cellular Immunology" (1980) Mishell, B. B. and Shügi, S. M. (eds) W. H. Freeman and Company, San Francisco) until about $10^7$ or more cells are obtained. Analysis of the cellular material can then be carried out by the above-mentioned method. For the purpose of the invention described herein, "mammalian" includes, but is not limited to, humans, monkeys, dogs, mice, hamsters and rats.

In another embodiment, the stimulation of cells in step (a) of the above-mentioned method comprises irradiating the cells for a time period and with a dose of ionizing radiation sufficient to induce or stimulate GADD45 mRNA expression. Ionizing radiation (IR) as used herein comprises a photon beam from a linear accelerator or gamma-radiation emitted by various radioisotopes. A preferred source of IR is gamma-irradiation emitted by a$^{137}$ cesium gamma-irradiator. Doses of IR effective to induce GADD45 mRNA expression range from about 2–20 Gray (Gy). A preferred time period and dose of IR effective to induce GADD45 mRNA expression is 20 Gy. Following IR stimulation cells are left in culture for about 1 to about 4 hours, preferably about 3 hours, prior to harvesting for use in the method. One skilled in the art will appreciate that various radiomimetic compounds (e.g. bleomycin) and DNA-damaging agents can also be used to stimulate the cells (Fornace, A. J. et al. (1992) *Annual Rev. of Genetics*, 26:505–524)

In step (b) of the method, RNA can be isolated from irradiated mammalian cells as whole cell RNA or as poly (A)$^+$ RNA. Whole cell RNA can be isolated by methods known to those skilled in the art. Such methods include extraction of RNA by differential precipitation (Birnboim, H. C. (1988) *Nucleic Acids Res.*, 16:1487–1497), extraction of RNA by organic solvents (Chomczynski, P. et al. (1987) *Anal. Biochem.*, 162:156–159) and extraction of RNA with strong denaturants (Chirgwin, J. M. et al. (1979) *Biochemistry*, 18:5294–5299). Poly(A)$^+$ RNA can be selected from whole cell RNA by affinity chromatography on oligo-d(T) columns (Aviv, H. et al. (1972) *Proc. Natl. Acad. Sci.*, 69:1408–1412). A preferred method of isolating RNA is extraction of whole cell RNA by acid-phenol (Chomczynski et al. 1987).

The methods for determining levels of cellular GADD45 mRNA expression to be compared in step (b) include Northern blotting (Alwine, J. C. et al. (1977) *Proc. Natl. Acad. Sci.*, 74:5350–5354), dot and slot hybridization (Kafatos, F. C. et al. (1979) *Nucleic Acids Res.*, 7:1541–1522), filter hybridization (Hollander, M. C. et al. (1990) *Biotechniques;* 9:174–179), RNase protection (Sambrook, J. et al. (1989) in "Molecular Cloning, A Laboratory Manual", Cold Spring Harbor Press, Plainview, N.Y.) and polymerase chain reaction (Watson, J. D. et al. (1992) in "Recombinant DNA" Second Edition, W. H. Freeman and Company, New York). A preferred method is the RNase protection assay.

The GADD45 nucleic acid sequence used as a probe for determining GADD45 mRNA expression is substantially homologous to human GADD45 cDNA (Papathanasiou et al. (1991) *Mol. Cell. Biol.*, 11:1009–1016). By "substantially homologous" is meant a level of homology between the nucleic acid sequence and the human GADD45 cDNA sequence. Preferably, the level of homology is in excess of 70%, more preferably in excess of 80%, with a particularly preferred nucleic acid sequence being in excess of 90% homologous with the human GADD45 clone.

The nucleic acid sequence can be labeled in single-stranded or double-stranded form. Labelling of the GADD45 nucleic acid sequence can be carried out by techniques known to one skilled in the art. Such labelling techniques can include radiolabels and enzymes (Sambrook, J. et al. (1989) in "Molecular Cloning, A Laboratory Manual", Cold Spring Harbor Press, Plainview, N.Y.). In addition, there are known non-radioactive techniques for signal amplification including methods for attaching chemical moieties to pyrimidine and purine rings (Dale, R. N. K. et al. (1973) *Proc. Natl. Acad. Sci.*, 70:2238–2242; Heck, R. F. (1968) *S. Am. Chem. Soc.*, 90:5518–5523), methods which allow detection by chemiluminescence (Barton, S. K. et al. (1992) *J. Am. Chem. Soc.*, 114:8736–8740) and methods utilizing biotinylated nucleic acid probes (Johnson, T. K. et al. (1983) *Anal. Biochem.*, 133:126–131; Erickson, P. F. et al. (1982) *J. of Immunology Methods*, 51:241–249; Matthaei, F. S. et al. (1986) *Anal. Biochem.*, 157:123–128) and methods which allow detection by fluorescence using commercially available products. A preferred method of labelling the GADD45 nucleic acid sequence is by synthesizing a $^{32}$P-labelled RNA probe by in vitro transcription of double-stranded GADD45 nucleic acid sequence using [α-$^{32}$P]UTP (Melton, D. A. et al. (1984) *Nucleic Acids Res.*, 12:7035–7056). The size of the probe can range from about 75 nucleotides to about 800 nucleotides. A preferred probe size is 269 nucleotides, spanning positions 296–565 of the human GADD45 cDNA (Papathanasiou et al. 1991).

In a second embodiment of the invention, the method to detect functional p53 comprises:

(a) stimulating mammalian cells to increase expression of GADD45 protein; and (b) comparing the level of GADD45 protein in stimulated cells to the level of GADD45 protein in unstimulated cells.

Examples of mammalian cells that can be used in the invention have been previously described herein. Examples of such cells include transformed mammalian cell lines and primary cultures of mammalian cells initiated from biopsies taken from mammalian tumors.

The stimulation of cells in step (a) of the above-mentioned method comprises irradiating the cells for a time period and with a dose of ionizing radiation (IR) sufficient to induce or stimulate expression of GADD45 protein. The source of IR used is the same as that described earlier for the stimulation of cells to increase GADD45 mRNA expression. Doses of IR effective to induce expression of GADD45 protein range from about 10 to about 20 GyO. Following IR stimulation, cells are left in culture for about 2 to about 16 hours, preferably about 4 hours, prior to harvesting for use in the method. Additional agents useful to induce or stimulate GADD45 mRNA and protein expression include, but are not limited to, UV radiation at from about 5 to about 20 Jm$^{-2}$, treatment with methyl methanesulfonate (MMS) at about 100 μg/ml for about 4 hours and by the placement of cells in $G_o$ via serum deprivation for about 24 to about 48 hours. One skilled in the art will also appreciate that, as described earlier, various radiomimetic compounds (eg bleomycin) and DNA-damaging agents can also be used to stimulate the cells. (Fornace, A. J. et al. (1992) *Annual Rev. of Genetics*, 26:505–524).

In step (b) of the method, protein extracts isolated from stimulated and unstimulated cells can be whole cell extracts or the whole cell extracts may be fractionated into nuclear or cytoplasmic extracts. (Dignam, J. D. et al. (1983) *Nucleic Acids Res.*, 11:1475–1489, Carrier, F. et al. (1992) *Mol. Cell. Biol.*, 12:1856–1863). Preferred protein extracts for use in the present method are nuclear extracts (Dignam, J. D. et al. (1983) *Nucleic Acids Res.*, 11:1475–1489, Carrier, F. et al. (1992) *Mol. Cell. Biol.*, 12:1856–1863).

The methods for determining levels of expression of GADD45 protein to be compared in step (b) include immunoassays known to one skilled in the art. Such immunoassays include, but are not limited to, immunoprecipitation, radioimmunoassay, Western blot assay, immunofluorescent assay, enzyme immunoassay, chemiluminescent assay, immunohistochemical assay and enzyme-linked immunosorbent assay (ELISA). In addition, the above immunoassays may be used in combination such as immunoprecipitation followed by Western blot. The above methods are described in *Principles and Practice of Immunoassay*, Price and Newman, eds., Stochton Press, 1991. Such assays may be a direct, indirect, competitive or noncompetitive immunoassay as described in the art (Oelbrick, n. (1984) *J. Clin. Chem. Clin. Biochem.*, 22:895–904).

The present invention also provides anti-GADD45 antibodies for use in the above immunoassays. Such antibodies may be polyclonal or monoclonal and it may be desirable to purify the antibodies before their use in the immunoassay. If polyclonal antibodies are desired, a selected mammal is immunized with a suitable immunogen. Serum from the immunized animal is collected and treated according to known procedures. If serum containing polyclonal antibodies to GADD45 protein contains antibodies to other antigens, the polyclonal antibodies can be purified by immunoaffinity chromatography (see Example 3). Alternatively, monoclonal antibodies directed against GADD45 can readily be produced by one skilled in the art. Methods of producing monoclonal or polyclonal antibodies are known to one skilled in the art (Goding, J. W. (1983) monoclonal antibodies: Principles and Practice, Plodermic Press, Inc., NY, N.Y., pp. 56–97; Hurn, B. A. L. et al. (1980) Meth. Enzymol. 70:104–141).

Suitable immunogens which may be used to produce the polyclonal or monoclonal antibodies of the present invention include cell lysate from cells transfected with a recombinant GADD45 protein or a partially or substantially purified recombinant GADD45 protein. Alternatively, the immunogen may be a partially or substantially purified nature GADD45 protein. Purification of the recombinant or native GADD45 protein can be accomplished by standard protein purification procedures known in the art which may include differential precipitation, molecular sieve chromatography, ion-exchange chromatography, isoelectric focusing, gel electrophoresis, affinity, and immunoaffinity chromatography and the like. In the case of immunoaffinity chromatography, the recombinant protein may be purified by passage through a column containing a resin which has bound thereto antibodies specific for the GADD45 protein.

In a preferred embodiment, the immunogen is a recombinantly produced GADD45 protein or fragments thereof. Production of recombinant GADD45 protein or a fragment thereof may be directed by a natural or synthetic nucleic acid sequence inserted into a suitable expression vector. A preferred nucleic acid sequence is the GADD45 cDNA sequence disclosed in Papathanasiou et al. (1991). In one embodiment, restriction digest fragments containing the full-length cDNA or fragments thereof containing a coding sequence for GADD45 can be inserted into a suitable expression vector. By suitable expression vector is meant a vector that can function in eukaryotic or prokaryotic cells and is capable of carrying and expressing a nucleic acid sequence encoding the GADD45 protein or a fragment thereof. Such vectors and their use in producing recombinant proteins are known to one skilled in the art (Sambrook, J. et al. (1989) in "Molecular Cloning, A Laboratory Manual", Cold Spring Harbor Press, Plainview, N.Y.). The production of a recombinant vector containing GADD45 nucleic acid sequence and its use in directing expression of recombinant GADD45 protein in bacteria is described in Example 3.

The immunogen of the present invention can be used in a suitable diluent such as saline or water, or in complete or incomplete adjuvants. Further, the immunogen may or may not be bound to a carrier to make the protein immunogenic. Examples of such carrier molecules include but are not limited to bovine serum albumin (BSA), keyhole limpet hemocyanin (KLH), tetanus toxoid, and the like. The immunogen can be administered by any route appropriate for antibody production such as intravenous, intraperitoneal, intramuscular, subcutaneous, and the like. The immunogen may be administered once or at periodic intervals until a significant titer of anti-HEV antibody is produced. The antibody may be detected in the serum using an immunoassay.

The antibodies or antigen binding fragments may also be produced by genetic engineering. The technology for expression of both heavy and light chain genes in *E. coli* in the subject of PCT patent applications; publication number WO 901443, WO 901443, and WO 9014424 and in Huse et al. (1989) *Science,* 246:1275–1281.

Alternatively, anti-GADD45 antibodies can be induced by administering anti-idiotype antibodies as immunogens. Conveniently, a purified anti-GADD45 antibody preparation prepared as described above is used to induce anti-idiotype antibody in a host animal. The composition is administered to the host animal in a suitable diluent. Following administration, usually repeated administration, the host produces anti-idiotype antibody. To eliminate an immunogenic response to the Fc region, antibodies produced by the same species as the host animal can be used or the FC region of the administered antibodies can be removed. Following induction of anti-idiotype antibody in the host animal, serum or plasma is removed to provide an antibody composition. The composition can be purified as described above for anti-GADD45 antibodies, or by affinity chromatography using anti-GADD45 antibodies bound to the affinity matrix.

Preferred antibodies for use in the present invention are polyclonal antibodies such as those described in Examples 3.

As noted earlier, the antibodies of the present invention may be used in immunoassays to determine the level of GADD45 protein in cells tissue culture cells or in biopsy samples. In a preferred embodiment, the antibodies are used in a Western blot assay as described in Example 4. After reaction of the GADD45 protein with anti-GADD45 antibody, unbound antibody is removed by washing and the antigen-antibody is reacted with a secondary antibody such as labelled anti-rabbit antibody. The label may be an enzyme which is detected by incubating the solid support in the presence of a suitable calorimetric or fluorimetric reagent. Other detectable labels may also be sued such as radiolabels or colloidal gold and the like.

In an alternative embodiment, the antibodies of the present invention can be used in situ to detect GADD45 protein in cells or tissues. In one embodiment, the antibodies are used in direct or indirect immunofluorescence. In the direct method, anti-GADD45 antibody labelled with a fluorescent reagent such as fluorescein isothiocyanate, rhodamine B isothiocyanate and the like is reacted directly with the GADD45 present in cells or tissues. In the indirect method, unlabelled anti-GADD45 antibody is reacted with the GADD45 protein present in cells or tissue. The unlabelled anti-GADD45 antibody is then reacted with a labelled second antibody. The second antibody can be labelled with a fluorescent tag as described above. The fluorescently labelled cells or tissues can then be detected using techniques known to one skilled in the art such as a fluorescence-activated cell sorter, light microscopy using a fluorescent light lamp and the like. Alternatively, GADD45 protein can be detected in situ via the use of radiolabelled anti-GADD45 antibody or via the use of an unlabelled anti-GADD45 antibody followed by a radiolabelled second antibody reactive to the anti-GADD45 antibody.

The antibodies of the present invention may also be used to immunoprecipitate the GADD45 protein from a mixture of proteins. The use of immunoprecipitation as a sensitive and specific technique to detect and quantitate target antigen in mixtures of proteins is well known to one skilled in the art (see Molecular Cloning, A Laboratory Manual, 2d Edition, Maniatis, T. et al. eds. (1989) Cold Spring Harbor Press).

The antibodies of the present invention may also be affixed to solid supports for use in the isolation of GADD45 by immunoaffinity chromatography. Techniques for immunoaffinity chromatography are known in the art (Harlow, E. and Lane, D. (1888) "Antibodies: A Laboratory Manual", Cold Spring Harbor Laboratory, Cold Spring Harbor, N.Y.) including techniques for affixing antibodies to solid supports so that they retain their immunoselective activity; the techniques used may be those in which the antibodies are adsorbed to the support as well as those in which the antibodies are covalently linked to the support. Generally, the techniques are similar to those used in covalent linking of antigen to a solid support; however, spacer groups may be included in the bifunctional coupling agents so that the antigen binding site of the antibody remains accessible.

The above described antibodies and antigen binding fragments thereof may be supplied in kit form alone or as a pharmaceutical composition for in vivo use. The antibodies may be used for therapeutic uses, for diagnostic use in immunoassays or as an immunoaffinity agent to purify GADD45 protein as described herein.

The present invention also provides a purified and isolated nucleic acid sequence having SEQ ID NO. 1 and a purified and isolated nucleic acid sequence having SEQ ID No. 2. SEQ ID NO. 1 and SEQ ID NO. 2 are complementary sequences found in the third intron of the human GADD45 gene and are set forth below:

TGGTACAGAA CATGTCTAAG CATGCTGGGG SEQ ID NO. 1

CCCCAGCATG CTTAGACATG TTCTGTACCA SEQ ID NO. 2

In a preferred embodiment, SEQ. ID NO. 1 and SEQ ID NO. 2 are synthetic oligonucleotides. Those skilled in the art would be aware that oligonucleotides can be synthesized by automated instruments sold by a variety of manufacturers or can be commercially custom-ordered and prepared.

In a preferred embodiment, SEQ ID NO. 1 and SEQ ID NO. 2 form a labelled, double-stranded nucleic acid sequence which binds to functional p53 and which is purified and isolated. The first and second strands can be labelled by using radiolabelled ATP and T4 polynucleotide kinase, radiolabelled nucleotides, and Klenow enzyme, (Sambrook, J. et al. (1989) in "Molecular Cloning, a Laboratory Manual", Cold Spring Harbor Press, Plainview, N.Y.) or by using any of the above-mentioned non-radioactive methods. A preferred method of labelling employed [γ-$^{32}$P] ATP and T4 kinase (Sambrook, J. et al. (1989)). SEQ ID NO. 1 and SEQ ID NO. 2 can anneal with each other to form double-stranded nucleic acid sequence by heating a mixture of the two sequences to 60°–90° C. for 5 to 30 minutes followed by cooling over 20 minutes to one hour to room temperature. A preferred method of annealing involves heating SEQ ID NO. 1 and SEQ ID NO. 2 at 65° C. for 5 minutes followed by slow cooling to room temperature over 30 minutes. The order of the labelling and annealing steps is not fixed; annealing can precede labelling or vice versa.

The present invention also relates to a method for determining the presence of functional p53 in mammalian cells by measuring binding of mammalian cell protein extract to a double-stranded nucleic acid sequence the previously-described said sequence comprising SEQ. ID NO. 1 and SEQ ID NO. 2, comprising:

(a) stimulating mammalian cells;

(b) binding the double-stranded nucleic acid sequence to protein extract prepared from stimulated and unstimulated cells; and (c) detecting complexes of protein extract bound to the double-stranded nucleic acid sequence.

A preferred stimulus of mammalian cells is ionizing radiation. Doses of ionizing radiation that can be used in this method range from about 5 to about 20 Gy. A preferred dose of ionizing radiation is 20 Gy. Following IR stimulation, cells are left in culture for about 1–4 hours, preferably about 3 hours, prior to harvesting for use in the method.

In one embodiment, the binding reaction of step (b) of the method can include from about 0.005 Ci to about 0.05 Ci of labelled double-stranded nucleic acid sequence and from about 2 to about 20 µg of protein extract. In a preferred embodiment, the binding reaction includes 0.005 Ci of labelled double-stranded nucleic acid sequence and 10 µg of protein extract. Types of protein extracts which are preferred are nuclear extracts (Dignam, J. D. et al. (1983) *Nucleic Acids Res.*, 11:1475–1489, Carrier, F. et al. (1992) *Mol. Cell. Biol.*, 12:1856–1863).

The binding of double-stranded nucleic acid sequence to protein extract can occur from 10 minutes to 2 hours at about 4° C.–37° C. Preferred conditions are for 20 minutes at room temperature. Methods useful to detect complexes of protein extract bound to double-stranded oligomer include mobility-shift analysis, Southwesterns, and immunoprecipitation (Sambrook, J. et al, (1989); Ausubel, J. et al, (1987) in "Current Protocols in Molecular Biology", John Wiley and Sons, New York). A preferred method is mobility-shift analysis using the double-stranded nucleic acid sequence labelled with [γ-$^{32}$P] ATP and T4 kinase. For mobility shift analysis, the protein extract-oligomer complexes can also be detected by using labelled protein extract, wherein the cells can be metabolically labelled with $^{125}$I, $^{35}$S, biotin and various fluorescent labels prior to the preparation of the protein extract.

The invention also provides a diagnostic kit for determining the presence of functional p53 in mammalian cells. This diagnostic kit comprises a purified and isolated nucleic acid according to SEQ ID NO. 1 and a purified and isolated nucleic acid sequence according to SEQ ID NO. 2.

Any articles or patents referenced herein are incorporated by reference. The following examples illustrate various aspects of the invention but are in no way intended to limit the scope thereof.

Materials

The materials used in the following Examples are as follows:

Cell Lines Embryonic fibroblasts from mice with manipulated p53 genes were obtained and characterized as previously described (Livingstone L. R. et al, (1992) *Cell*, 70:923–935). Other cell types utilized were previously described (Kastan et al, (1991a); Kuerbitz, et al, (1992)).

Plasmid Clones The following cDNA clones were used: pXR45m, a nearly full-length Chinese hamster gadd45 clone (Papathanasiou et al, (1991) and pA2, a 1.2 kb Chinese hamster β-actin clone. The plasmid pGAPD4 contained an insert spanning positions 256–359 of the human glyceraldehyde-3-phosphate dehydrogenase cDNA (GenBank/EMBL Accession No. M17851) that was subcloned between the HindIII and EcoRI sites of pGEM7zf.

The plasmid pRibo-Hg45 consisted of a 269 bp fragment spanning positions 296–565 of the human gadd45 cDNA (Papathanasiou et al, (1991) that was subcloned between the EcoRI and SmaI sites of pBluescript II SK.

EXAMPLE 1

Dependence of Induction of GADD45 mRNA by Ionizing Radiation on the Presence of Functional p53

The GADD45 gene has previously been found to be inducible by ionizing radiation (IR) in normal human fibroblasts and lymphoblasts but not in some tumor cell lines (Papathansiou, M. A. et al., (1991)). In an effort to identify genes that may be induced by p53 after ionizing radiation, the response of the GADD45 gene was examined in human cells where the p53 phenotype is known. Human cell lines with a wild-type p53 phenotype (FIG. 1A) or a mutant or null p53 phenotype (FIG. 1B) or primary fibroblasts from mice with the designated p53 genotype (FIG. 1C) were maintained in culture and exposed to 20 Gy of ionizing radiation for 3 hours prior to harvest as previously described (Kastan, M. B. et al. (1991a); Kuerbitz, S. J. et al. (1992) Proc. Natl. Acad. Sci., 89:7491–7495). Cells were harvested by lysing them in 4M guanidine thiocyanate. Whole-cell RNA was then isolated by the acid phenol method (Chomczynski, P. et al. (1987)).

Figure 1B:
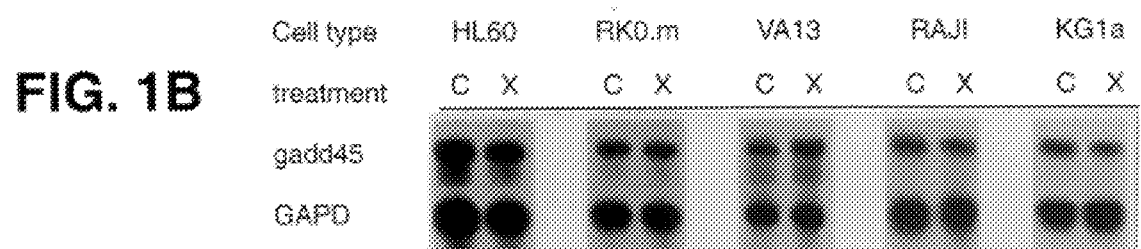
Figure 1C:
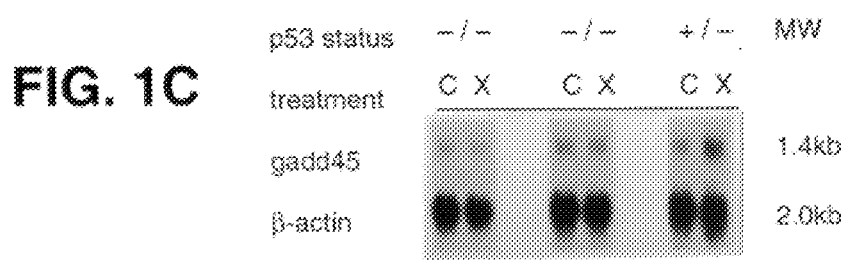

For FIGS. 1A and 1B, isolated RNA was analyzed by RNase protection assays. Reagents for these assays were obtained from Ambion, Inc., and the procedure was similar to that supplied by the manufacturer with only minor modifications. In brief, the plasmids pRibo-Hg45 and pGAPD4 were linearized with HindIII or BamHI respectively, and in vitro transcription was carried out at 4° C. for 1 hr with T3 or T7 RNA polymerase, respectively. GADD45 and GAPD riboprobes were labeled with [$\alpha$-$^{32}$P]UTP at 14 or 15 Ci/mmol, respectively. 10 $\mu$g of whole-cell RNA was hybridized with both riboprobes simultaneously (in the same test tube) at 53° C. for 15 hr and then digested with RNase A and RNase T1. Following proteinase K digestion and phenol/chloroform extraction, the samples were analyzed on a 8M urea/5% acrylamide gel. Protected bands were visualized by autoradiography and were quantified with a Betascope (Betagen, Inc.). The relative level of GADD45 mRNA was determined by normalizing the Betascope counts (minus background) for GADD45 to that of GAPD for each sample.

When mRNA levels were determined in this fashion, a clear increase for GADD45 was observed in cells with a wild-type p53 phenotype while the control transcript GADD was unchanged (FIG. 1A). In contrast, appreciable induction GADD45 of GADD45 mRNA was not evident in cells lacking a wild-type p53 phenotype (FIG. 1B).

Analysis of the RNA isolated from primary fibroblasts (FIG. 1C) was done by Northern blot since RNAse protection requires a homologous probe and the only rodent probe available for GADD45 is from hamster. In brief, samples of whole cell RNA (10 $\mu$g) were size separated and hybridized with a hamster GADD45 probe; the blot was stripped and then hybridized with a hamster $\beta$-actin probe (Fornace, A. J. et al., (1989b)). Only the hybridizing bands are shown with the estimated sizes (Kb) to the right. The results clearly show that an increase in GADD45 mRNA levels following IR treatment failed to occur in the murine embryonic fibroblasts in which the p53 genes had been disrupted by homologous recombination (p53 status –/–) while the heterozygous cells with only one intact wild-type p53 allele still remaining (p53 status +/–) still induced GADD45 mRNA following IR treatment (NOTE: +/+ cells were not available in sufficient quantities for this experiment). Thus, the dependence of the induction of GADD45 mRNA by ionizing radiation on the presence of wild-type p53 is observed not only in cells of hematopoietic origin (FIG. 1A) but also in non-hematopoietic cells such as fibroblasts.

EXAMPLE 2

Relationship of p53 Functional Status to GADD45 Induction in Cell Lines Having Normal or Abnormal p53 Function In order to further examine the relationship of p53 functional status to GADD45 mRNA induction, the magnitude of this induction was measured in numerous cell lines having normal p53 function (8 cell lines) or abnormal p53 function (7 cell lines).

TABLE 1

Fold increase of GADD45 mRNA after $\gamma$-irradiation

| Cell Line | Cell type | p53 status | $\gamma$-ray $G_1$ arrest[a] | Relative Abundance of mRNA[b] |
|---|---|---|---|---|
| Normal p53 function | | | | |
| ML-1 | myeloid Leukemia | wt/wt | + | 9.9 |
| U2-OS | osteosarcoma | wt/wt | + | 3.0 |
| AG1522 | skin fibroblast | wt/wt | ND | 4.2 |
| 344 | skin fibroblast | wt/wt | + | 3.3 |
| WI38 | lung fibroblast | wt/wt | ND | 2.0 |
| RKO | colorectal carcinoma | wt/wt | + | 3.1 |
| RKO.cp[c] | colorectal carcinoma | wt/wt | + | 3.2 |
| RKO.c[d] | colorectal carcinoma | wt/wt | + | 4.1 |
| Abnormal p53 function | | | | |
| RKO.m[e] | colorectal carcinoma | wt/wt, cut | – | 1.4 |
| Raji | lymphoid leukemia | wt/mut | – | 0.7 |
| SW480 | colorectal carcinoma | mut/– | – | 1.4 |
| KG1a | myeloid leukemia | mut/– | – | 0.8 |
| HL60 | myeloid leukemia | –/– | – | 1.0 |
| VA13 | lung fibroblast | ?, SV40 transformed | ND | 1.0 |
| HeLa | cervical carcinoma | wt/wt, HPV-18 infected | ± | 1.6 |

[a]Activation of arrest in the $G^1$ phase of the cell cycle following $\gamma$-irradiation as published previously (Kastan et al., (1991a); Kuerbitz et al., 1992); ND, not tested.
[b]Relative values for samples harvested 4 hr. after 20 Gy compared to untreated controls as determined by RNAse protection assay (see Experimental Procedures).
[c]Polyclonal population, transfected with control vector lacking p53 gene insert (Kuerbitz et al, 1992)
[d]Clonal population, transfected with control vector lacking p53 gene insert (Kuerbitz et al, 1992)
[e]Clonal population, transfected with mp53 vector RKO.p53.13; Kuerbitz et al, 1992)
[f]Measurable decrease in S-phase, but markedly less than cells with normal p53 function All cell lines were cultured and treated with 20 Gy ionizing radiation 3 hours prior to the harvest of the cells as described previously (Kastan, M. B. et al. (1991), Kuerlitz, S. J. et al. (1992)). Total RNA was isolated and analyzed by RNAse protection assay as described in Example 1. This analysis was done in a blinded fashion with the identity of the cell types withheld until all quantitations were completed.

The relative abundance of GADD45 mRNA in irradiated cells was estimated by first normalizing to the value for GAPD in each sample and then dividing this value for irradiated cells by that of its control. Normal lymphoblasts and fibroblasts, and tumor cells with a wt p53 status all exhibited greater than 2-fold increases in GADD45 mRNA after irradiation, with a range up to 10-fold. Induction of GADD45 mRNA also correlated with the activation by ionizing radiation of the $G_1$ checkpoint in these cells, which have normal p53 function (Kastan, M. B. et al. (1991), Kuerbitz, S. J. et al. (1992)). In contrast, cells with mutant (SW480, Raji, and KG1a) or absent (HL60) p53 genes failed to show appreciable induction of GADD45 mRNA after IR (Table 1). Loss of GADD45 responsiveness after IR also correlated with loss of the $G_1$ checkpoint (Table 1) and loss of induction of p53 protein (Kastan, M. B. et al. (1991a), Kuerbitz, S. J. et al. (1992)).

The basal levels of GADD45 mRNA did not correlate with p53 status and were low in all cells. It was estimated that the abundance of GADD45 mRNA was >100-fold lower than that of GAPD mRNA in these cell lines. The relative levels of GAPD mRNA could be accurately estimated by quantitative dot-blot hybridization using whole-cell RNA and normalized to the polyA content of the cells. When this was done (data not shown), this value was used to compute the relative level of GADD45 mRNA in different cell types (also employing the values in Table 1), and to confirm that the level of GAPD mRNA remained constant after IR.

Cells with wt p53 genes, but expressing viral products that interfere with p53 function, similarly lacked normal IR-mediated GADD45 induction. VA13 is a derivative of WI38 that was obtained by transformation with SV40 (Girardi, A. J. et al. (1966) *Ann. Med. Exp. Biol. Fern.,* 44:242–254). The T antigen of this virus is known to bind to p53 protein (Lane, D. P. et al. (1979)), and VA13 cells were deficient in induction of GADD45 mRNA (Table 1). Hela cells have been infected with HPV-18 which contains an E6 protein that inhibits normal p53 function (Werness, B. A. et al. (1990), Scheffner, M. et al. (1990) *Cell,* 63:1129–1136; Scheffner, M. et al. (1991) *Proc. Natl. Acad. Sci.,* 88:5523–5527; Crook, T. et al. (1991) *Cell,* 67:547–556). Activation of the $G_1$ checkpoint and induction of GADD45 was substantially less in HeLa cells than in the cell lines with normal p53 function (Table 1).

To demonstrate that it was the status of the p53 gene and not some other difference between these cell lines which was responsible for the differences in gadd45 induction, gadd45 induction was evaluated in cells in which the p53 gene had been manipulated. RKO colorectal carcinoma cells stably over expressing a mutant (codon 143) p53 gene have previously been shown to lose the $G_1$ arrest following IR (Kuerbitz, S. J. et. al. (1992)). In contrast to parental RKO cells (FIG. 1A) and RKO cells transfected with a control vector lacking the p53 gene insert, RKO cells over expressing the mutant p53 allele did not significantly increase GADD45 mRNA levels following IR (Table 1).

EXAMPLE 3

Production of Anti-GADD45 Antibodies

Construction of recombinant GADD45 Expression Vector. oligonucleotide primers containing an NdeI (SEQ ID NO:3) and a BamHI (SEQ ID NO:4) restriction site respectively were synthesized. The nucleic acid sequences of SEQ ID NO:3 and SEQ ID NO:4 are shown below:

GGTGCCAAGC ATATGACTTT GGAGGAATTC
T                                    SEQ ID NO:3

GGTGCCAAAG ATCTTCACCG
TTCAGGGAGA TTA                       SEQ ID NO: 4

Polymerase chain raction (PCR) was then carried out using SEQ ID NO:3 and SEQ ID NO:4 as primers in order to amplify the cDNA encoding the open reading frame of GADD45 (Papathanasion et al. (1991)). The nucleic acid sequence of the resulting amplified GADD45-cDNA insert contained an NdeI site on the 5' end and BamHI site at the 3' end. The nucleic acid sequence of the GADD45 insert and its encoded amino acid sequence are shown in FIG. 2. Following introduction of SEQ ID NOS:3 and 4 into GADD45 cDNA by PCR, the GADD45 insert shown in FIG. 2 was then inserted into the NdeI-Bam HI sites of the pET-14b vector (Novagen, Madison, Wis.) such that expression of the GADD45 cDNA was placed under the control of the inducible lac UV5 promoter. The insertion of the GADD45 insert into the pET-14b vector resulted in DNA sequence encoding a histidine tag being placed at the 5' end (amino terminus) of the GADD45 insert. The recombinant GADD45 vector was carried and amplified in HB101 (GIBCO-BRL, Gaithersburg, Md.) bacterial strains.

Expression of Recombinant GADD45 Protein in Bacteria.

Figure 3:
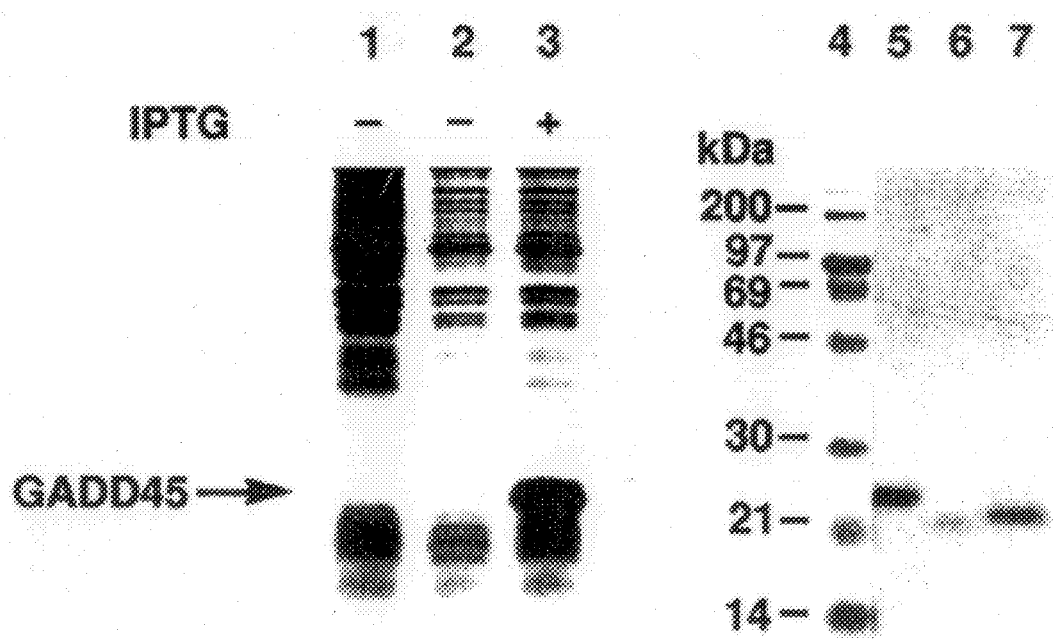
FIG. 3 shows a sodium dodecyl sulfate polyacrylamide gel (SDS-PAGE) in which cell lysates of untransfected bacteria (lane 1), cell lysates of bacteria transfected with the recombinant GADD45 vector (lanes 2 and 3), or purified GADD45 with (lane 5) or without (lanes 6 and 7) a 6 amino acid N-terminal histidine tag were stained with Coomasie blue. Lane 4 contains protein size markers. As indicated at the top of FIG. 3, the cell lysate in lane 3 was obtained from bacteria induced with isopropyl β-D-thiogalactopyranoside (IPTG) while the cell lysates in lanes 1 and 2 were obtained from bacteria that had not been induced with IPTG.

The recombinant GADD45 vector was transfected into competent bacterial strain BL-21 (Novagen) by heat shock at 42° C. (Sambrook et al. (1989)). The recombinant protein was induced by addition of 0.4 mM IPTG to the bacterial solution. After induction, the bacteria were centrifuged and the pellet was resuspended in binding buffer (5 mM imidazole, 0.5M NaCl, 20 mM Tris-Hcl, (pH 7.9). The suspension was sonicated, centrifuged and applied on a His-Bind affinity column (Novagen) according to the manufacturer's protocol. The column was washed and eluted with buffer containing 1M imidazole (pH 7.9)). The eluted proteins were dialyzed against phosphate-buffered saline (PBS) and concentrated on centriprep-10 (Amicon, Beverly, Mass.). The histidine tag on the N-terminus of the protein was removed by proteolytic cleavage with thrombin (Novagen) which reduced the size of the recombinant protein by 2 kDa (FIG. 3).

Immunization of Rabbits

The resultant GADD45 recombinant protein without the Histidine Tag was used to immunize 6 New-Zealand rabbits. Six white female New-Zealand rabbits at each 6–8 lbs were divided into two groups of three rabbits each. Two immunization protocols were used. For the first set of rabbits (FC-4, 5, 6) the first injection (1 mg of recombinant GADD45 protein) was prepared with complete Freund's adjuvant and multiple subcutaneous injections were made. The rabbits were then boosted at weeks 5, 8, 10, and 11 with 100 μg of protein in incomplete Freund's adjuvant by injection into the lymph nodes. The immunized rabbits were then first bled on week 12 and bled every three weeks thereafter. Serum titer from each bleed was tested against recombinant protein on slot blot analysis (Sambrook et al. (1989)) followed by Western blot.

The second set of rabbits (FC-7, 8, 9) received for their first injection multiple subcutaneous injections of 1 mg of recombinant GADD45 protein in complete Freund's adjuvant. The animals were then boosted every three weeks with 1 mg of protein in incomplete Freund's adjuvant via multiple subcutaneous injections. The rabbits were bled by the ear every three weeks and serum titers were checked with recombinant protein on slot blot.

Purification of Anti-GADD45 Antibody.

One mg of recombinant GADD45 protein was covalently bound to an agarose activated support using the AminoLink kit (Pierce, Rockford, Ill.) Activated aldehydes on the agarose matrix react with primary amine groups of the proteins to form Schiff bases. Serum obtained from rabbit FC-5 was then applied to the column and unbound proteins were washed out with phosphate-buffered saline, (PBS). The bound IgG were eluted with 0.1M Glycine (pH 2.8). Fractions containing the eluted proteins were pooled, neutralized with Tris-base and dialyzed against PBS.

EXAMPLE 4

Detection by Western Blot of IR-Induced GADD45 Protein Expression in Mammalian Cells In order to determine whether the relationship of p53 functional status to GADD45 mRNA induction by ionizing radiation extends to induction of GADD45 protein, Western blot analysis of nuclear and cytoplasmic protein extracts isolated from unirradiated and γ-irradiated human colorectal cells was performed as follows using anti-GADD45 IgG. Human colorectal carcinoma (RKO) cells (wild-type cells having normal p53 function) were grown and maintained as described in Zhan et al. (Mol. Cell. Biol., (1993) 13:4242–4250.). Cells were irradiated as previously described (Hollander, M. C., and Fornace, A. J., Jr. Cancer Res. (1989) 49:1687–1692), except that radiation was from a $^{137}$Cs source at a dose of 5.5 Gy/min. Following IR stimulation, the cells were left in culture for 1, 2, 3, 4, 8 and 16 hours prior to harvesting. Nuclear and cytoplasmic protein extracts were then obtained as previously described (Carrier et al. Mol. Cell. Biol. (1992) 12:1856–1863.). Protein concentrations of the nuclear and cytoplasmic extracts were determined using BioRad protein dye according to the manufacturer's directions (BioRad, Bethesda, Md.). Protein (100 ug/lane) from nuclear) and cytoplasmic protein extracts were electrophoresed on a 12.5% polyacrylamide-sodium dodesyl sulfate (SDS-PAGE) gels and transferred onto nitrocellulose with a semi-dry blotter (BIO-RAD, Melville, N.Y.). The blots were then incubated with 0.2 μg/ml of purified anti-GADD45 IgG for 3 hours at room temperature. After 3 hours blots were washed and incubated with a second antibody, anti-rabbit alkaline phosphatase conjugate, (Promega, Madison, Wis.) at a dilution of 1:10,000 for 1 h at room temperature. Protein detection was performed with a chemiluminescence kit (TROPIX, Bedford, Mass.) according to the manufacturer's recommendation. The results of the blots are shown in FIG. 4 where the upper panel shows the blot of nuclear extracts and the lower panel shows the blot of cytoplasmic extracts. Detectable levels of GADD45 protein were not observed in cytoplasmic extracts isolated from either irradiated or unirradiated cells (lower panel). By comparison, a clear increase in the level of GADD45 protein was observed in nuclear extracts isolated from irradiated cells (upper panel). Thus, these results show that GADD45 protein levels, like GADD45 mRNA levels, are induced by ionizing radiation treatment of cells having normal p53 function.

EXAMPLE 5

Demonstration of Binding of Endogenous p53 to a Double-Stranded Oligomer Containing a p53-Binding Element Found in the GADD45 Gene In order to determine whether endogenous p53 could bind to a double-stranded oligomer containing a conserved p53-binding sequence located in the 3rd intron of the human GADD45 gene, mobility-shift assays were carried out using a double-stranded oligonucleotide corresponding to a putative p53-binding site located in the third intron of the human GADD45 gene and nuclear extracts from γ-irradiated cells. In brief, cells were irradiated with a $^{137}$cesium source at 5.5 Gy/min and nuclear extracts were prepared as described previously (Dignam et al, (1983); Carrier et al, 1992). DNA-binding reactions were carried out for 20 min at room temperature in a buffer containing 20 mM N-2-hydroxyethylpiperazine-M'-2-ethanesulfonic acid (HEPES) (pH 7.8), 100 mM KCl, 1 mM EDTA, 1 mM dithiothreitol, 0.5 μg of sonicated salmon sperm DNA, $10^4$ dpm of labeled probe, 10% glycerol and 10 μg of nuclear protein extract. The probe used was a 30-mer double-stranded synthetic oligonucleotide comprising two synthetic oligonucleotides containing SEQ. ID. No. 1 and SEQ. ID. No. 2, respectively. Each oligonucleotide was radioactively labeled with $[\gamma-^{32}P]$ ATP and T4 kinase (Sambrook, J. et al, (1989)) and the labelled oligomers were ethanol precipitated, washed with 70% ethanol and either allowed to auto-anneal or to anneal with each other by incubation at 65° C. for 5 minutes in 50 mM Tris, pH 7.6/10 mM $MgCl_2$/1 mM ATP/1 mM DTT/5% (w/v) polyethylene glycol-8000, followed by slow cooling over 30 minutes to room temperature. The annealed DNA was extracted with phenol/chloroform, ethanol precipitated, washed with 70% ethanol and resuspended in 3 mM Tris, pH 7.5/0.2M EDTA. Where indicated, 0.2 μg of monoclonal anti-p53 antibodies (Oncogene Science, Manhasset, N.Y.) (PAb421 or PAb1801) were added prior to the addition of nuclear extract. PAb421 IgG was purified from ascites fluid on protein-A agarose (ImmunoPure Plus, Pierce, Rockford, Ill.); PAb1801 IgG (Oncogene Science, Manhasset; N.Y.) was used directly. The samples were then analyzed on a 4% non-denaturing acrylamide gel (Carrier et al, 1992).

Figure 5B:
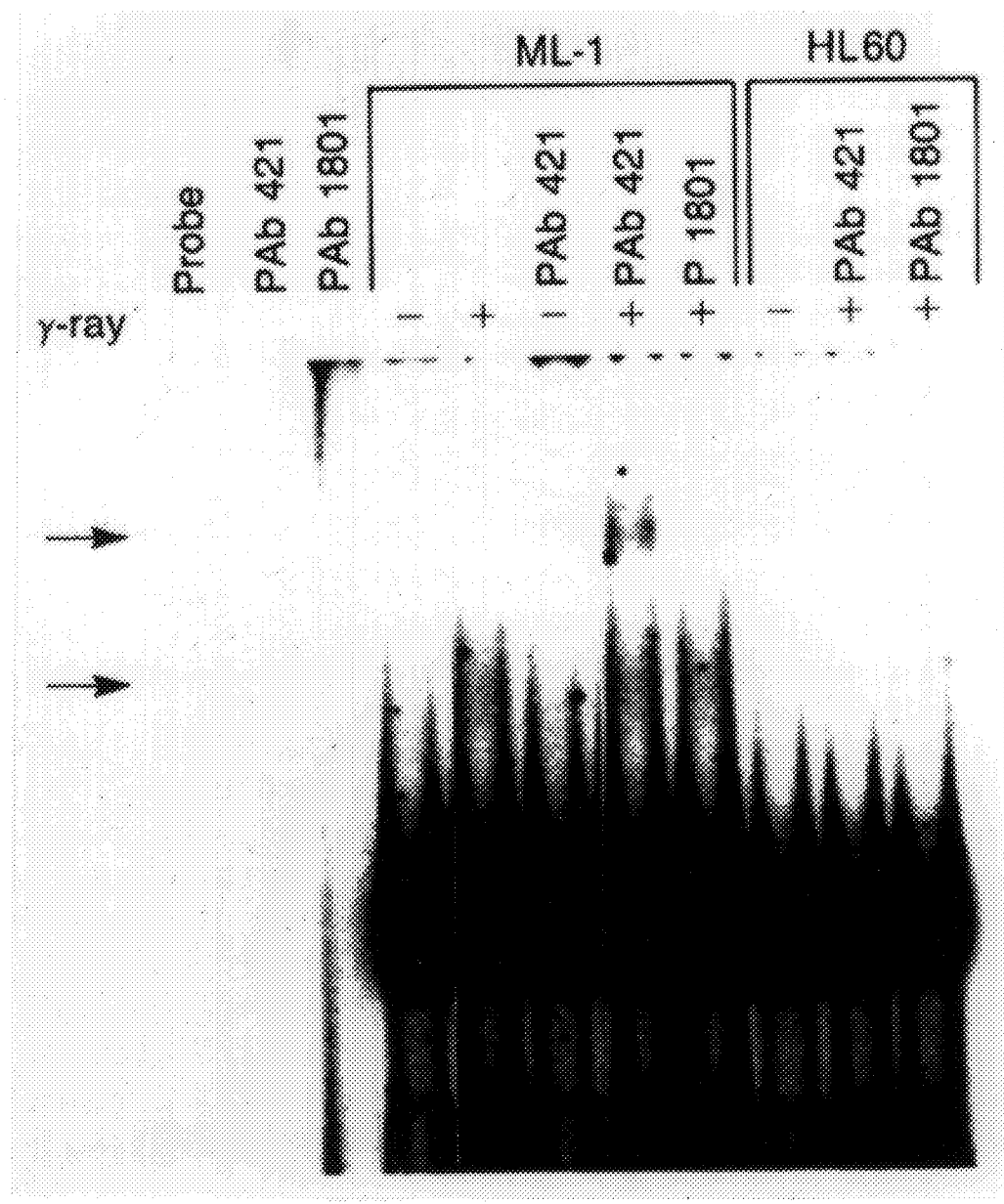

The results show that in extracts from unirradiated ML-1 cells, several bands are evident—some of which may represent constitutive DNA-binding proteins; however, a distinct band (lower arrow, FIG. 5A) which is clearly visible in the IR extract is not detected in the extract from untreated cells. With the inclusion of the PAb421 antibody to p53, a higher "super-shifted" band is observed (upper arrow). Interestingly, as was found previously (Funk, W. D. et al. (1992)) with other p53-binding oligomers and p53 protein produced by an expression vector, the p53 antibody PAb1801, which binds to the amino terminus of p53 protein (in contrast to the carboxyl terminal binding of PAb421 (Wade-Evans, A. et al. (1985) *Embo. J.*, 4:699–706), did not produce a super-shifted band. The reason for this difference in the antibodies is uncertain. In a second similar experiment (FIG. 5B), results without nuclear extracts and with extracts from HL60 cells were compared to those from ML-1 cells. In contrast to ML-1 cells, neither the induced band or the super-shifted band are apparent in extracts from irradiated HL60 cells, which have a null p53 genotype. In addition to using the antibodies and the HL-60 cells, the specificity of p53 binding in these experiments was further demonstrated by blocking both shifted bands with addition of excess unlabeled identical oligomer (data not shown). These results indicate that an IR-inducible nuclear factor, which binds to the GADD45 p53 site, is present in ML-1 cells, and that this factor contains p53. This is the first demonstration of binding of an endogenous p53 gene product to a specific DNA sequence.

EXAMPLE 6

Determination of the Functional Status of p53 in Mammalian Cell Tumors

The functional status of p53 in mammalian cells can be determined by measuring increases in cellular GADD45 mRNA and/or protein levels after ionizing radiation and/or binding of endogenous p53 to a double-stranded oligomer containing a conserved p53-binding element found in the human GADD45 gene. Biopsies of lymphoid and myeloid tumors from laboratory were obtained by surgical excision or incision. Primary cultures of mammalian cells can be initiated from biopsies by removal of adequate amounts of viable tumor tissue under sterile conditions. The number of cells required to initiate one or more cell culture lines is determined empirically for each tumor but in many cases, a needle biopsy containing about $10^6$ to about $10^8$ cells is sufficient. Once the cell culture lines are initiated, they can be grown on a short-term basis (from about 2 days to about 20 days) using standard culture techniques ("Selected Methods in Cellular Immunology", (1980) Mishell, B. B. and Shiigi, S. M. (eds), W. H. Freeman and Company, San Francisco). About $10^7$ or more cells from such cultures are necessary to allow direct determination of the presence of functional p53 in these tumor cells by stimulation with ionizing radiation as described in Example 1. Whole cell RNA is isolated and analyzed by RNase protection assay in order to determine whether GADD45 mRNA increased in response to the ionizing radiation.

In addition, or in the alternative, nuclear protein extracts are isolated and analyzed by Western blot using anti-GADD45 antibody in order to determine whether GADD45 protein increased in response to the ionizing radiation. An observed increase in GADD45 mRNA/protein levels in stimulated vs. unstimulated tumor cells indicates that functional p53 is present in the tumor cells while no change in the levels of GADD45 mRNA/protein indicates that the tumor cells exhibit abnormal p53 function.

Alternatively, tumor cell culture lines can be analyzed for the presence of functional p53 by mobility-shift analysis as described in Example 3 of nuclear extracts prepared from these cultures. About $10^7$ or more cells is adequate for preparation of nuclear extract.

We claim:

1. A method for determining the presence of functional p53 in mammalian cells by measuring GADD45 protein expression, comprising the steps of:
   (a) stimulating the mammalian cells to increase GADD45 protein expression by irradiating said cells with ionizing radiation or with a radiomimetic compound in an amount sufficient to stimulate GADD45 protein expression; and
   (b) comparing the level of GADD45 protein in said stimulated cells to the level of GADD45 protein in unstimulated cells.

2. The method of claim 1, wherein the dose of ionizing radiation sufficient to stimulate GADD45 protein expression is 10 to 20 Gy.

3. The method of claim 1, wherein said comparison step includes the steps of:
   (a) providing an anti-GADD45 antibody; and
   (b) contacting GADD45 protein with said antibody.

4. The method of claim 3 wherein said contacting step further includes isolating nuclear protein extract from stimulated and unstimulated cells.

5. The method of claim 3, wherein said GADD45 protein is contacted with said antibody in a Western blot assay.

6. The method of claim 3, wherein said GADD45 protein is contacted with said antibody in an immunoprecipitation assay.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TGGTACAGAA CATGTCTAAG CATGCTGGGG                                                                                                    3 0

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CCCCAGCATG CTTAGACATG TTCTGTACCA                                                                                                    3 0

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GGTGCCAAGC ATATGACTTT GGAGGAATTC T                                                                                           3 1

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GGTGCCAAAG ATCTTCACCG TTCAGGGAGA TTA                                                                          3 3